(12) United States Patent
Cloutier et al.

(10) Patent No.: US 10,299,704 B2
(45) Date of Patent: May 28, 2019

(54) METHOD FOR MONITORING OF ACTIVITY AND FALL

(71) Applicant: Christian Cloutier, St-Elzear (CA)

(72) Inventors: Christian Cloutier, Saint-Elzear (CA); Régis Fortin, Laval (CA)

(73) Assignee: GROUPE EVERCLOSE INC., St-Elzéar (CA)

( * ) Notice: Subject to any disclaimer, the term of this patent is extended or adjusted under 35 U.S.C. 154(b) by 0 days.

(21) Appl. No.: 15/446,503

(22) Filed: Mar. 1, 2017

(65) Prior Publication Data

US 2017/0172464 A1   Jun. 22, 2017

Related U.S. Application Data

(62) Division of application No. 11/297,368, filed on Dec. 9, 2005, now Pat. No. 9,615,777.

(30) Foreign Application Priority Data

Dec. 9, 2004  (CA) ..................................... 2486949

(51) Int. Cl.
| | | |
|---|---|---|
| *A61B 5/00* | (2006.01) | |
| *A61B 5/11* | (2006.01) | |
| *G08B 21/02* | (2006.01) | |
| *G08B 21/04* | (2006.01) | |

(52) U.S. Cl.
CPC .......... *A61B 5/1117* (2013.01); *A61B 5/0002* (2013.01); *A61B 5/0022* (2013.01); *A61B 5/1118* (2013.01); *A61B 5/4818* (2013.01); *A61B 5/681* (2013.01); *G08B 21/0288* (2013.01); *G08B 21/0415* (2013.01); *G08B 21/0446* (2013.01); *A61B 2562/0219* (2013.01)

(58) Field of Classification Search
CPC .. A61L 35/11; A61L 35/1117; A61L 35/1118; A61L 35/0002; A61L 35/4818; A61L 2562/0219; G08B 21/0288; G08B 21/0415; G08B 21/0446
See application file for complete search history.

(56) References Cited

U.S. PATENT DOCUMENTS

| | | |
|---|---|---|
| 4,110,741 A | 8/1978 | Hubert et al. |
| 4,829,285 A | 5/1989 | Brand et al. |
| 4,858,622 A | 8/1989 | Osterwell |
| 5,008,654 A | 4/1991 | Callaway |
| 5,045,839 A | 9/1991 | Ellis et al. |

(Continued)

FOREIGN PATENT DOCUMENTS

| | | |
|---|---|---|
| CA | 2275959 | 7/1998 |
| CA | 2399182 | 8/2001 |

(Continued)

*Primary Examiner* — Max Hindenburg
(74) *Attorney, Agent, or Firm* — Bereskin & Parr LLP/S.E.N.C.R.L.,s.r.l.

(57) ABSTRACT

A method for monitoring activity of a subject in an environment, comprising providing at least one sensing assembly in the environment of the subject; providing a server communicating with at least one of: i) the subject and ii) the at least one sensing assembly; generating property vectors from data collected by the at least one sensing assembly; characterizing activity of the subject from the property vectors; and having a result of said characterizing step accessible to the server.

22 Claims, 9 Drawing Sheets

(56) References Cited

U.S. PATENT DOCUMENTS

| | | | |
|---|---|---|---|
| 5,146,206 A | 9/1992 | Callaway | |
| 5,317,305 A | 5/1994 | Campman | |
| 5,398,019 A | 3/1995 | Barnett et al. | |
| 5,402,107 A | 3/1995 | Rencavage | |
| 5,515,858 A | 5/1996 | Myllymaki | |
| 5,544,661 A | 8/1996 | Davis et al. | |
| 5,670,944 A | 9/1997 | Myllymaki | |
| 5,682,882 A | 11/1997 | Lieberman | |
| 5,751,214 A | 5/1998 | Cowley et al. | |
| 5,774,055 A | 6/1998 | Pomerantz | |
| 5,853,005 A | 12/1998 | Scanlon | |
| 5,919,149 A | 7/1999 | Allum | |
| 5,955,667 A | 9/1999 | Fyfe | |
| 5,963,891 A | 10/1999 | Walker et al. | |
| 6,047,203 A * | 4/2000 | Sackner | A41D 13/1281 600/301 |
| 6,048,324 A | 4/2000 | Socci et al. | |
| 6,102,856 A | 8/2000 | Groff et al. | |
| 6,148,280 A | 11/2000 | Kramer | |
| 6,160,478 A | 12/2000 | Jacobsen et al. | |
| 6,166,644 A | 12/2000 | Stroda | |
| 6,198,394 B1 | 3/2001 | Jacobsen et al. | |
| 6,201,476 B1 | 3/2001 | Depeursinge et al. | |
| 6,208,251 B1 | 3/2001 | Cadet et al. | |
| 6,239,704 B1 | 5/2001 | Olsen | |
| 6,265,978 B1 | 7/2001 | Atlas | |
| 6,307,481 B1 | 10/2001 | Lehrman et al. | |
| 6,433,690 B2 | 8/2002 | Petelenz et al. | |
| 6,501,386 B2 | 12/2002 | Lehrman et al. | |
| 6,567,485 B1 | 5/2003 | Venier | |
| 6,570,503 B1 | 5/2003 | Ulert et al. | |
| 6,572,560 B1 | 6/2003 | Watrous et al. | |
| 6,582,380 B2 | 6/2003 | Kazlausky et al. | |
| 6,611,783 B2 | 8/2003 | Kelly, Jr. et al. | |
| 6,661,347 B2 | 12/2003 | Lehrman et al. | |
| 6,703,939 B2 | 3/2004 | Lehrman et al. | |
| 6,774,795 B2 | 8/2004 | Eshelman et al. | |
| 7,150,048 B2 * | 12/2006 | Buckman | A41D 13/018 2/465 |
| 9,615,777 B2 * | 4/2017 | Cloutier | A61B 5/0002 |
| 2001/0004234 A1 | 6/2001 | Petelenz et al. | |
| 2001/0021814 A1 | 9/2001 | Schomburg | |
| 2001/0032059 A1 | 10/2001 | Kelly et al. | |
| 2001/0048368 A1 | 12/2001 | Lehrman et al. | |
| 2002/0008630 A1 | 1/2002 | Lehrman et al. | |
| 2002/0116080 A1 | 8/2002 | Birnbach et al. | |
| 2002/0118121 A1 | 8/2002 | Lehrman et al. | |
| 2003/0018430 A1 | 1/2003 | Ladetto et al. | |
| 2003/0093003 A1 | 5/2003 | Watrous et al. | |
| 2003/0139692 A1 | 7/2003 | Barrey et al. | |
| 2003/0153836 A1 | 8/2003 | Gagnadre et al. | |
| 2004/0010390 A1 | 1/2004 | Kelly, Jr. et al. | |
| 2004/0015103 A1 | 1/2004 | Aminian et al. | |
| 2004/0021569 A1 | 2/2004 | Lepkofker et al. | |

FOREIGN PATENT DOCUMENTS

| | | |
|---|---|---|
| EP | 0877346 | 11/1998 |
| EP | 1128349 | 8/2001 |
| EP | 1195139 | 4/2002 |
| WO | 0069517 | 11/2000 |
| WO | 03065891 | 8/2003 |

* cited by examiner

Fig_11

Fig. 12

METHOD FOR MONITORING OF ACTIVITY AND FALL

CROSS REFERENCE TO RELATED APPLICATIONS

This application is a divisional of U.S. patent application Ser. No. 11/297,368, which itself claims priority on Canadian application no. CA 2,486,949, filed on Dec. 9, 2004. All documents above are herein incorporated by reference.

FIELD OF THE INVENTION

The present invention relates to monitoring of a subject. More specifically, the present invention is concerned with a method for monitoring of activity and fall of a subject.

SUMMARY OF THE INVENTION

More specifically, there is provided a method for monitoring activity of a subject in an environment, comprising providing at least one sensing assembly in the environment of the subject; providing a server communicating with at least one of: i) the subject and ii) the at least one sensing assembly; generating property vectors from data collected by the at least one sensing assembly; characterizing activity of the subject from the property vectors; and having a result of said characterizing step accessible to the server.

Other objects, advantages and features of the present invention will become more apparent upon reading of the following non-restrictive description of embodiments thereof, given by way of example only with reference to the accompanying drawings.

DESCRIPTION OF EMBODIMENTS OF THE INVENTION

Figure 1:
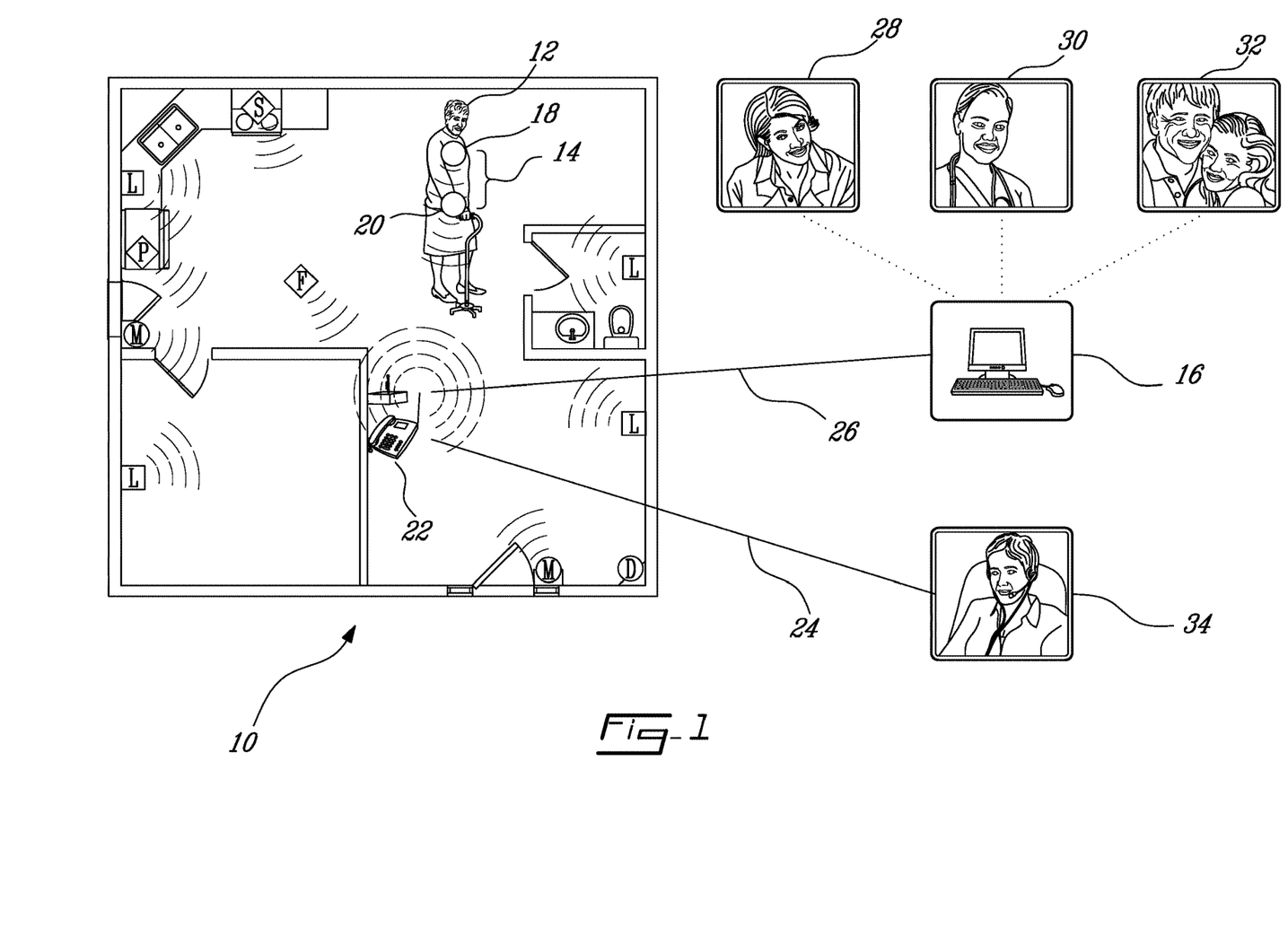
FIG. 1 is a diagram of a first embodiment of a system according to the present invention.

A system as illustrated in FIG. 1 comprises a sensing assembly 14 and a server 16, a subject to be monitored 12 being in its environment 10.

The sensing assembly 14 illustrated in the embodiment of FIG. 1 comprises a first sensor unit 18, located in the region of the neck of the subject 12, for example integrated in a neck assembly worn by the subject 12, and a second sensor unit 20 located in the region of the diaphragm, or/and the fist and/or of the leg of the subject 12, for example in a wrist band.

The sensor units include at least one 2- or 3-axes accelerometers. They may further comprise a gyroscope. The respective number, combination and location of the different sensors depend on target monitoring data, as will be explained hereinbelow.

For example, the first sensor unit 18 may comprise a high G accelerometer and a low G accelerometer, while the second unit sensor 20 comprises a low G accelerometer, both optionally further comprising a gyroscope.

Alternatively, the sensor unit 18, located at the base of the neck of the subject 12, integrated in a neck assembly that the subject 12 wears, may comprise a three-axes high G sensor and a gyroscope. The sensor unit 20, worn as a bracelet, comprises a low G accelerometer and a gyroscope. The sensing assembly 14 communicates with a base 22, located in the environment 10 of the subject 12. This base 22 is connected by a phone link 24 and by Internet 26 to a server 16 for information exchange. Access to the remote server 16 is controlled and allows target persons, such as a physician 28, employees of a health center 30, members of the family 32 of a human subject 12 for example, as well as a call center 34 to monitor data and profiles corresponding to the subject 12 from a distance. The remote server 16 is also used as an interface for sending messages and instructions to the different parts of the system.

The system automatically detects falls and critical activity levels of the subject 12 and is able to emit a request for intervention or alarm, as will be further described hereinbelow.

The base 22 may support a remotely modifiable and programmable reminder function useful for assisting subjects with a cognitive deficiency, whereby remote-intervention functions are allowed. The base 22 may also comprise means for processing data and alarms received from the sensing assembly 14, as well as means for bi-directional voice communication. It may further support a mobile unit of the wireless type offering similar features as just described and optionally integrating GPS localization means allowing monitoring the subject 12 outdoors for example.

Figure 2:
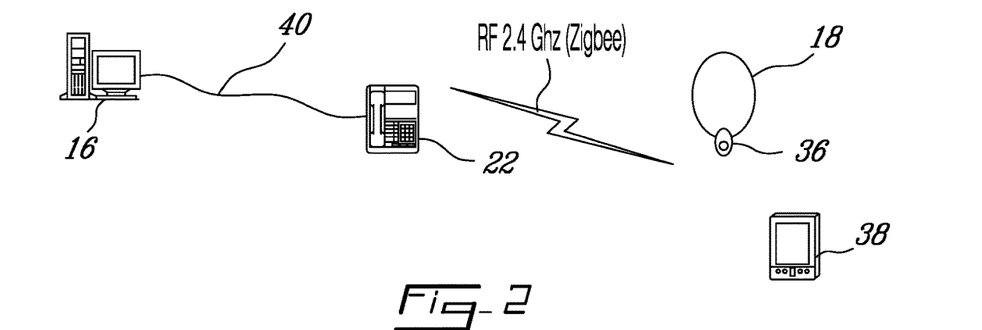
FIG. 2 is a diagram of a second embodiment of a system according to the present invention.

In the embodiment illustrated in FIG. 2, the sensor assembly 14 consists of a sensor unit 18 comprising a 3-axes high G sensor and a gyroscope, integrated in a neck assembly worn by the subject 12. The neck assembly comprises RF communication means to the base unit 22, and a device for asking help 36. The base 22 is a hands-free unit allowing wireless communication, through a 2.4 GHz RF link of a ZIGBEE® network for example, to the neck assembly and optional detectors 38. The base 22 includes a help button and a reset button. The base 22 is linked to a remote server 16 by standard telephone network 40.

Figure 3:
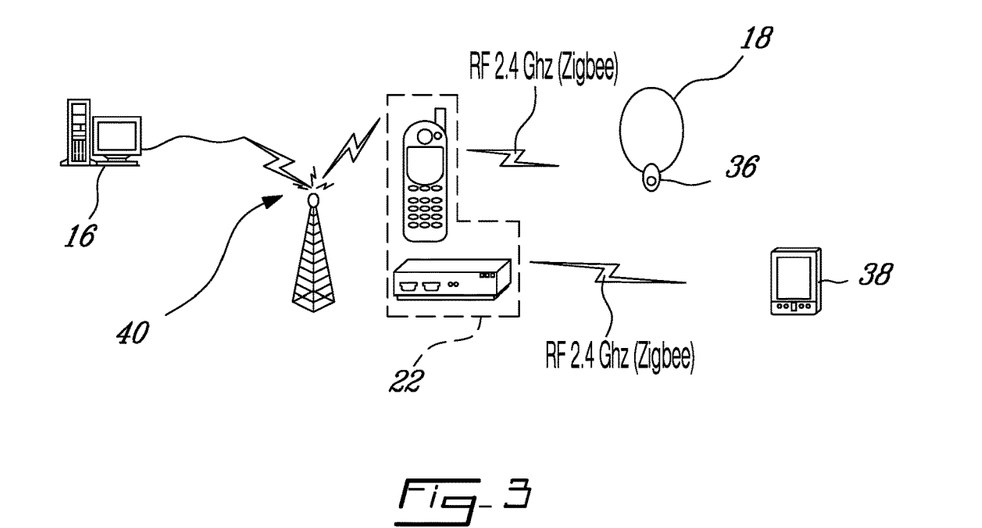
FIG. 3 is a diagram of a third embodiment of a system according to the present invention.

In the embodiment illustrated in FIG. 3, the base 22 is a free-hands phone allowing wireless communication with the sensor unit 18 and optional detectors 38 on the one hand, and to a remote server 16 via a cellular network 40 on the second hand.

As exemplified in FIG. 1, optional detectors 38 may include for example three-dimensional locaters and interphones (L), motion sensors (M) and presence detectors (D), pillbox sensor (P), smoke detectors (F) and household-appliance detectors (S).

Figure 4:
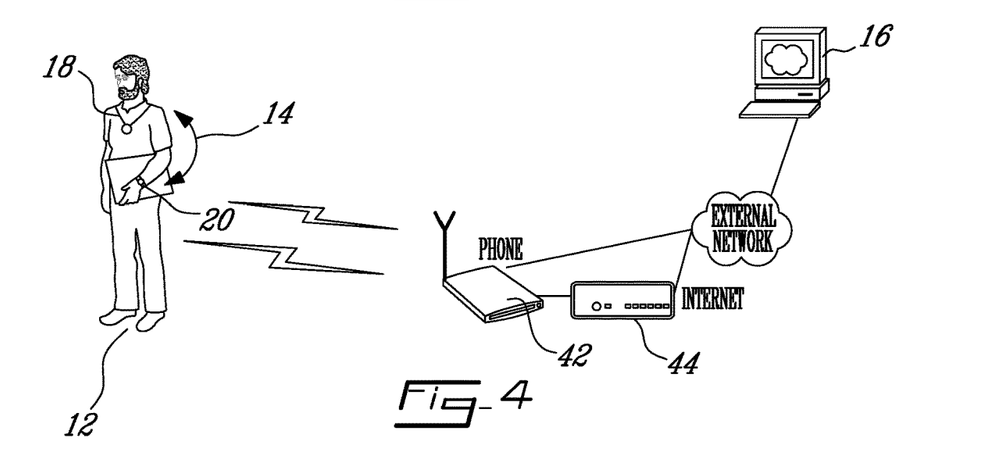
FIG. 4 is a diagram of a fourth embodiment of a system according to the present invention.

In the embodiment illustrated in FIG. 4, the subject 12 wears a first sensor unit 18 as a neck assembly and a second sensor unit 20 as a wristband. Both sensor units are connected by a unidirectional low frequency low power RF communication link. The sensor unit 20 is connected to a 900 MHz bidirectional receiver 42. The receiver 42, connected to a modem cable or DSL 44, sends data in case of alarm to, or transfer data upon request of, a remote server 16, using an external network accessed either by phone and/or by the Internet.

Figure 5:
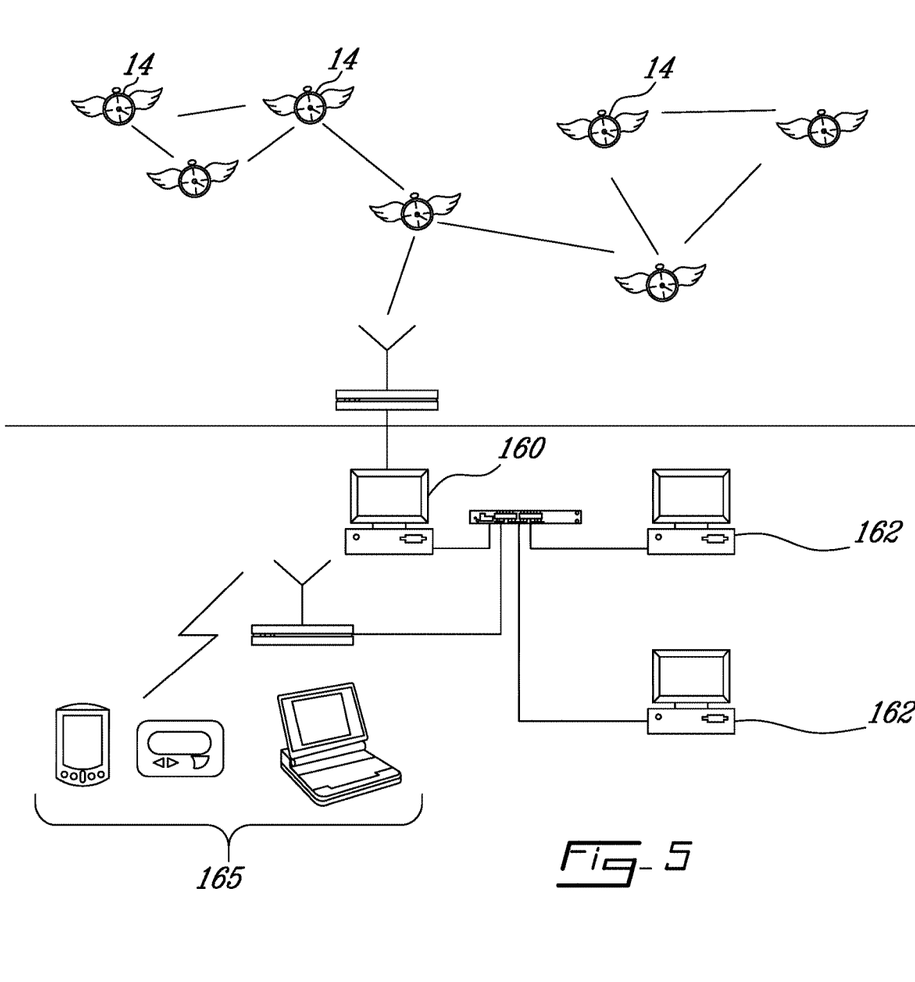
FIG. 5 is a diagram of a fifth embodiment of a system according to the present invention.

In the embodiment illustrated FIG. 5, a plurality of sensing assemblies 14 are arranged as a 900 MHz network of a local network type for example, for monitoring a plurality of subjects, for example in a shelter for elderly in the case of human subjects, or a herd. The resulting network of sensing assemblies 14 is linked to a central server 160 connected to other servers 162 used for accessing information provided by the central server 160, and connected to mobile units 165 by a wireless network.

These systems allow collecting data related to the dynamics of the movements of least one subject to be monitored.

The sensor unit 18 in the upper part of the body of a person being monitored, or in the front part of an animal being monitored for example, typically comprises a high G accelerometer to detect fall of the subject. It may further comprise a low G accelerometer to follow the position of movements of the subject. The frequency, velocity and space orientation of movements of the upper trunk of the subject is used to yield movement levels, which can be graded from null to intense. These parameters may be processed using a variety of tools such as fuzzy logic, threshold parameters or a weighting mechanism for example.

For example, energy levels may be obtained as an average of the sum of the absolute values of acceleration along the three axes of the 3 axis accelerometer for example, corrected by an offset characterizing the sum of these accelerations at rest (since accelerometers measure not only the energy involved during a movement of the person, but also the gravitational force the person is submitted to), over a number of measurements per second. This off set is to be taken into account, considering that acceleration generated by a moving person is within the range between about −2 G and +2 G on a one second cycle basis, while the gravitational force is generally about 9.8 m/s/s, i.e. the signal corresponding to the gravitational force may be stronger than those corresponding to the person's movements.

In a particular embodiment, the energy level (NE) are thus obtained as follows: the OG (offset) value of each accelerometer is measured acceleration along the three axes thereof, by placing each axis in perfect alignment with the direction of the gravitational force, yielding the values $X_{offset}$, $Y_{offset}$ and $Z_{offset}$. In practice, the offset values may be set during the fabrication stage of the accelerometer, for example by making the OG value correspond to an octet value of 128 (the octet 0 being related to −5 G, and the octet 255 corresponding to +5 G). The energy level NE is calculated as the average over 142 vectorials modules $NE_i$ during a period of one second, 142 being the number of sample by second samples, wherein each vectorial module $NE_i$ is the square root of the sum of the squared corrected values axes. A new NE value is generated every second and stored. This indicator NE allows quantifying the intensity of movements thus provides energy levels over periods of 1, 5, 30 minutes or more.

A second indicator NM, may be used to quantify the movement levels, describing in particular movements of low amplitude. A detector having a maximum and a minimum on each axis of the accelerometer is used, on 1-second periods of time. By subtracting this minimum to that maximum, the offset is obtained. The NM value is generated and stored simultaneously with the NE.

A gain KM for the movement level NM and a gain Ke for the energy level NE may be defined and used to generate an indicator of movement level.

A third indicator, referred to as INC, may be used to identify a fall event, as detected by an impact sensor, by comparison to an adjustable threshold. The impact sensor measures a gradient and amplitude of shock waves related to a fall, typically characterized by 10 waves over 0.25 seconds. The fall indicator INC may be defined as the sum of absolute values of amplitudes measured during an event. Typically, an INC of 25% corresponds to low amplitude impacts, while severe falls are characterized by INC values of 100% and more.

Such data may further be used to determine sub-levels of sleeping activity, including sleep phases and intensity, or levels of low-intensity activities such as rest or writing process.

The sensor assembly of the present invention allows identifying critical levels of activity, as defined according to a target population of subjects to be monitored, such as persons suffering from functional dependence for example. Critical levels may be set for a range of activities, including a total lack thereof such as in case of death, breathing rhythms and apnea, breathing in absence of minimal movement such as in case of coma or faintness, and hyperactivity.

A preliminary classification of the persons to be monitored according to their degree of physical sufficiency allows setting threshold and control parameters adapted individually to each of these persons and to yield data all the more representative of the state of each one of them.

Nycthemeral or circadian analysis may be used to obtain activity patterns of a subject for time monitoring and identification of abnormal or undesirable variations in time of the subject.

Activity of the subject may be qualitatively assessed, be it walking, feeding or sleeping for example, by analyzing the data collected by the sensing assembly of the system by processing based on neural networks in combination with fuzzy logics or logic threshold values, depending on the processing and memory capacity available.

As described hereinabove, the present system, using at least one sensing assembly comprising at least one a high G accelerometer, may be used for monitoring a fall of this subject and a low-G one for monitoring his-her activity level. Turning to FIGS. 6 to 10 of the appended drawings, embodiments of a method according to the present invention method will now be described.

Figure 6:
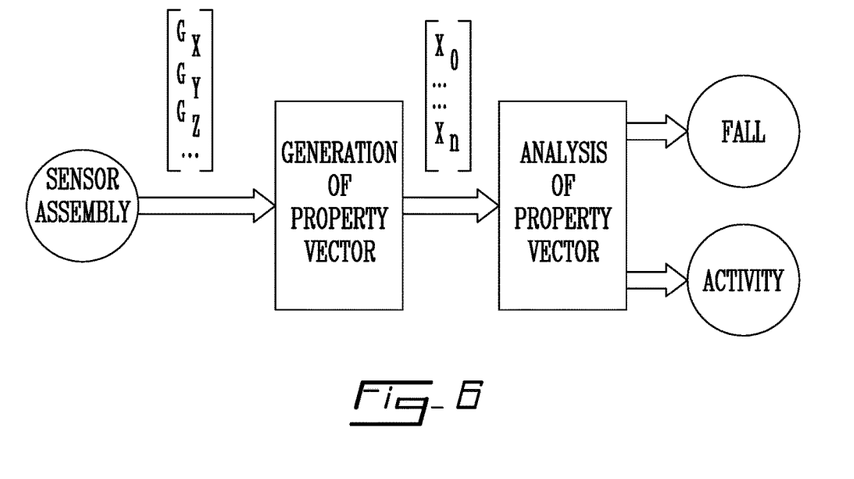
FIG. 6 a flowchart of an embodiment of a method according to the present invention.
Figure 7:
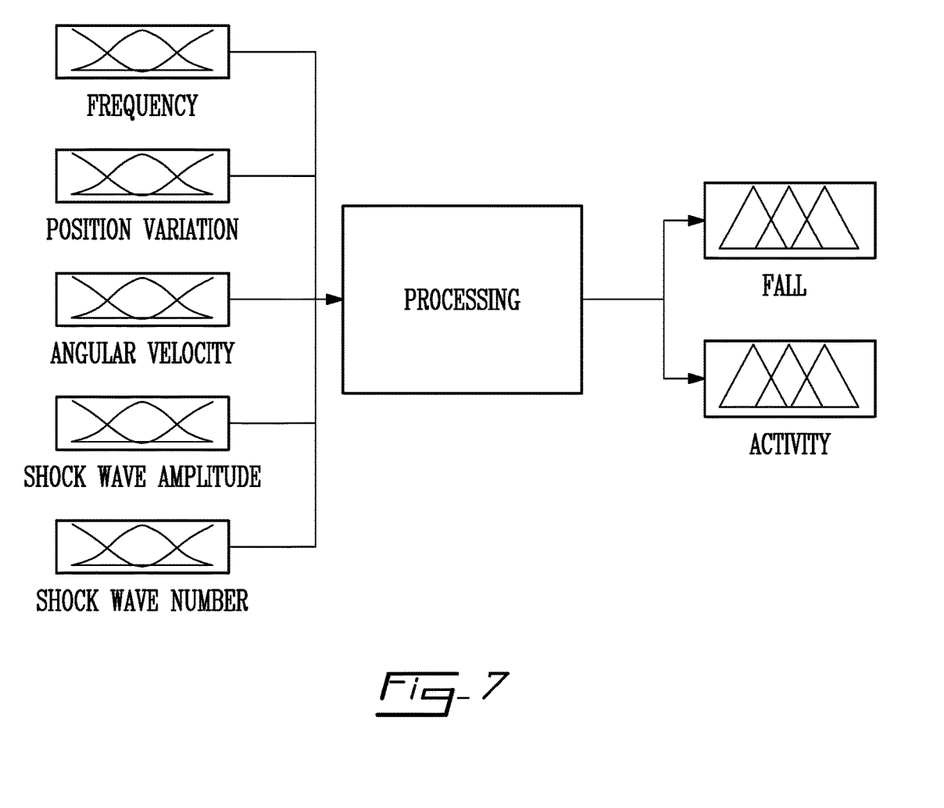
FIG. 7 is a flowchart of another embodiment of a method according to the present invention.
Figure 8:
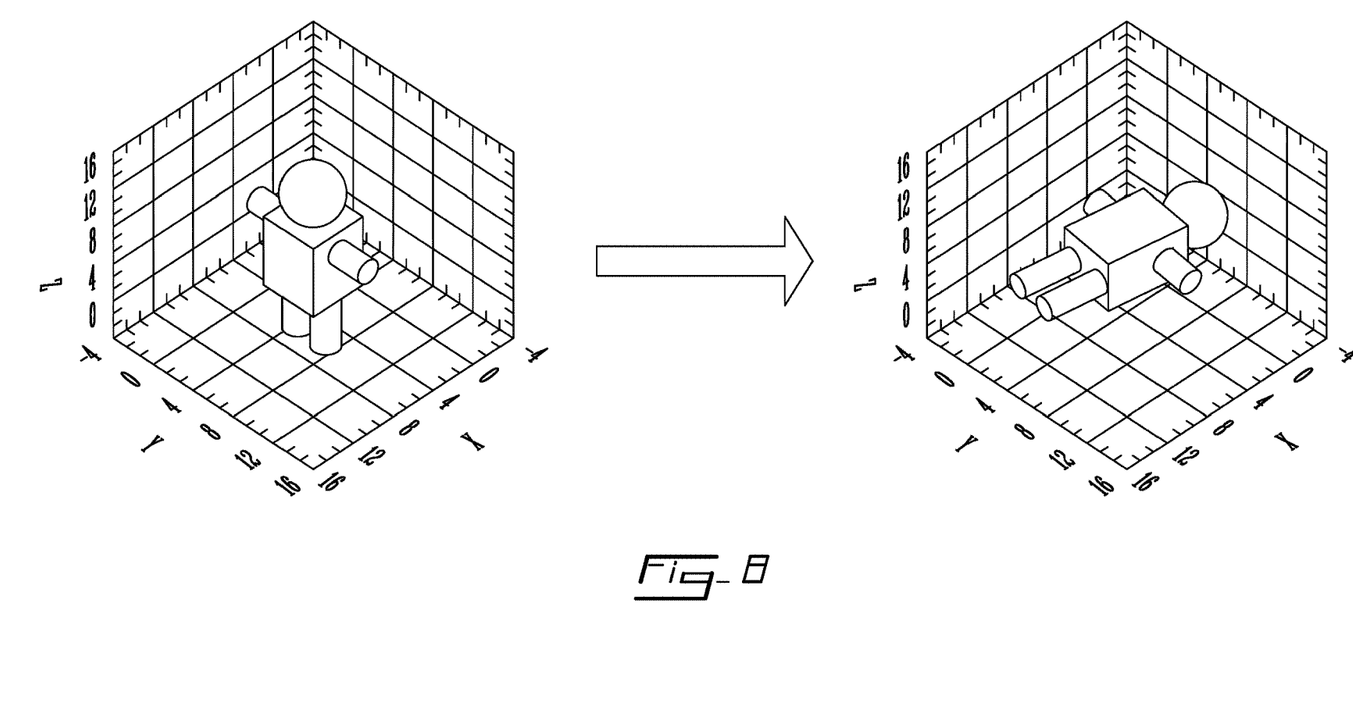
FIG. 8 is a diagram of positioning obtained by a method according to the present invention.

In FIG. 6, for example, the sensing assembly provides analog signals emitted by at least a 3-axes accelerometer and two gyroscopes. These signals are digitized by an analog-to-digital converter. The obtained data are placed in a memory stack storage used as a short-term memory, and which size defines the term in seconds. Low-level algorithms are applied to the data of the memory stack storage to extract data on the behavior and body posture of the subject being monitored, by generating a property vector from these data. Such property vector includes a number of parameters as follows (see FIG. 7):

frequency of the body movement, defining the activity of the monitored subject by the absence of activity, the rest, moderate and active awaken states;

trunk position variation: data collected by the accelerometer allow determining the space orientation of the accelerometer, which is related to the space orientation (x, y, z) of the monitored subject, through gravity and knowledge of the location of the accelerometer in relation to the body of the monitored subject (see FIG. 8);

height of the monitored subject along a z direction, which may be used to sort out actual fall events from false alarms by correlating this height with the position of the body (see FIG. 8);

angular velocity of the trunk of the monitored subject, which may be used to determine whether a trunk position variation results from a controlled movement or from an accidental movement;

shock wave amplitude, characterizing a fall event;

number of shock waves, which may be used to sort out actual fall events from false alarms.

As shown in FIG. 8, the position of the monitored subject includes his-her position along a vertical axis (noted z in the Figure), which allows assessing the height of an event taking place in a (x,y) plane, i.e. determining whether the monitored subject is lying on the floor, lying on top of a bed, seated, kneeling down, or standing. Measuring the position along the vertical axis may be achieved by RFID (radio frequency identification), ultrasound or using a camera for example.

The property vector is analyzed to determine whether the monitored subject has fallen and to yield indications on the type of activities the subject is involved in. Fuzzy logics analysis may for example be used to yield to output information, relating to fall and activity respectively.

Using a sensing assembly comprising a sensor unit in the upper part of the subject combining a high frequency-low accuracy (high G in the range of 100 G) accelerometer and a low frequency-high accuracy (low G in the range between 2 and 5 G) accelerometer, allows detecting events such as impact as well as body posture and fine movements.

Moreover, the locations of the sensor units of the sensing assembly relative to the monitored subject's body may be selected to combine a sensor unit at the wrist of the monitored subject with a sensor unit in the region of the base of the neck for example. The combination of these sensor units allows tracking the dynamics of the trunk of the monitored subject while allowing discarding non-pertinent interferences due to non-significant movements for example. Furthermore, this combination allows detecting a fall event while reducing false-alarms generation, since, for example in the case of a single wrist sensor unit, even a knock of the hand wearing the wrist sensor unit on a table for example would be detected as an impact.

Such a combination of the locations of the sensor units allows sorting events, by allowing a validation between impacts or movements usually of lower amplitude of the trunk of the monitored subject and impacts or movements usually of higher amplitude of the arm of the monitored subject. It further allows a qualitative assessment of events, by allowing for example to identify a movement of the arm alone as a protection movement.

The sensor unit in the region of the trunk of the monitored subject may be efficiently connected to the monitored subject without use of straps, since a neck assembly for example may be used, as described earlier hereinabove.

A gyroscope included in the sensor unit located at the base of the neck or trunk of the monitored subject allows measuring angular velocities, i.e. velocity of lateral movements (left to right and right to left) and back and forth movements of the trunk of the monitored subject. Moreover, data from such gyroscope are used to determine threshold values of angular velocities.

Figure 9:
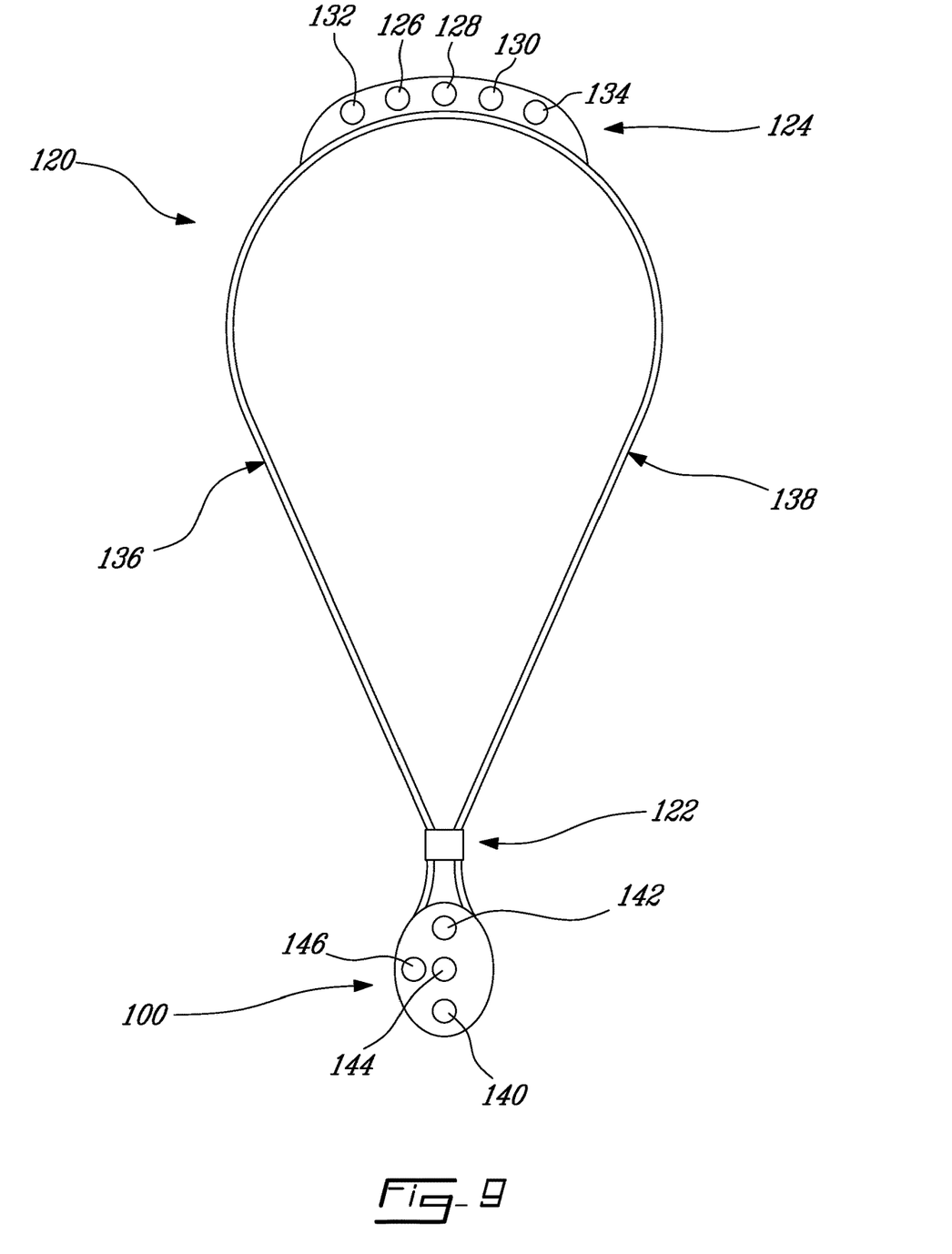
FIG. 9 illustrates an embodiment of a neck assembly according to the present invention.

FIG. 9 illustrates an embodiment of a neck assembly 120 of a bolo tie type for locating a sensor unit. A clip 122, besides allowing adjusting a length of the assembly 120 around the neck of the person to be monitored, acts as a balancing weight securing the assembly 120 in place as the monitored person moves. The region of the assembly 120 placed in the back of the neck comprises a flexible unit 124 housing sensors, including a 2-5 G accelerometer 128 and a 50 G accelerometer 126, and optionally a gyroscope 134, a thermistor 130, and an impedance detector 132 for monitoring wearing of the assembly. The assembly 120 comprises an RF antenna 138 and a link 136 between the flexible unit 124 and a pendant 100. The pendant 100 houses a microphone 140, a 3D positioning unit 142, a help summon button 144 and a battery 146.

Figure 10:
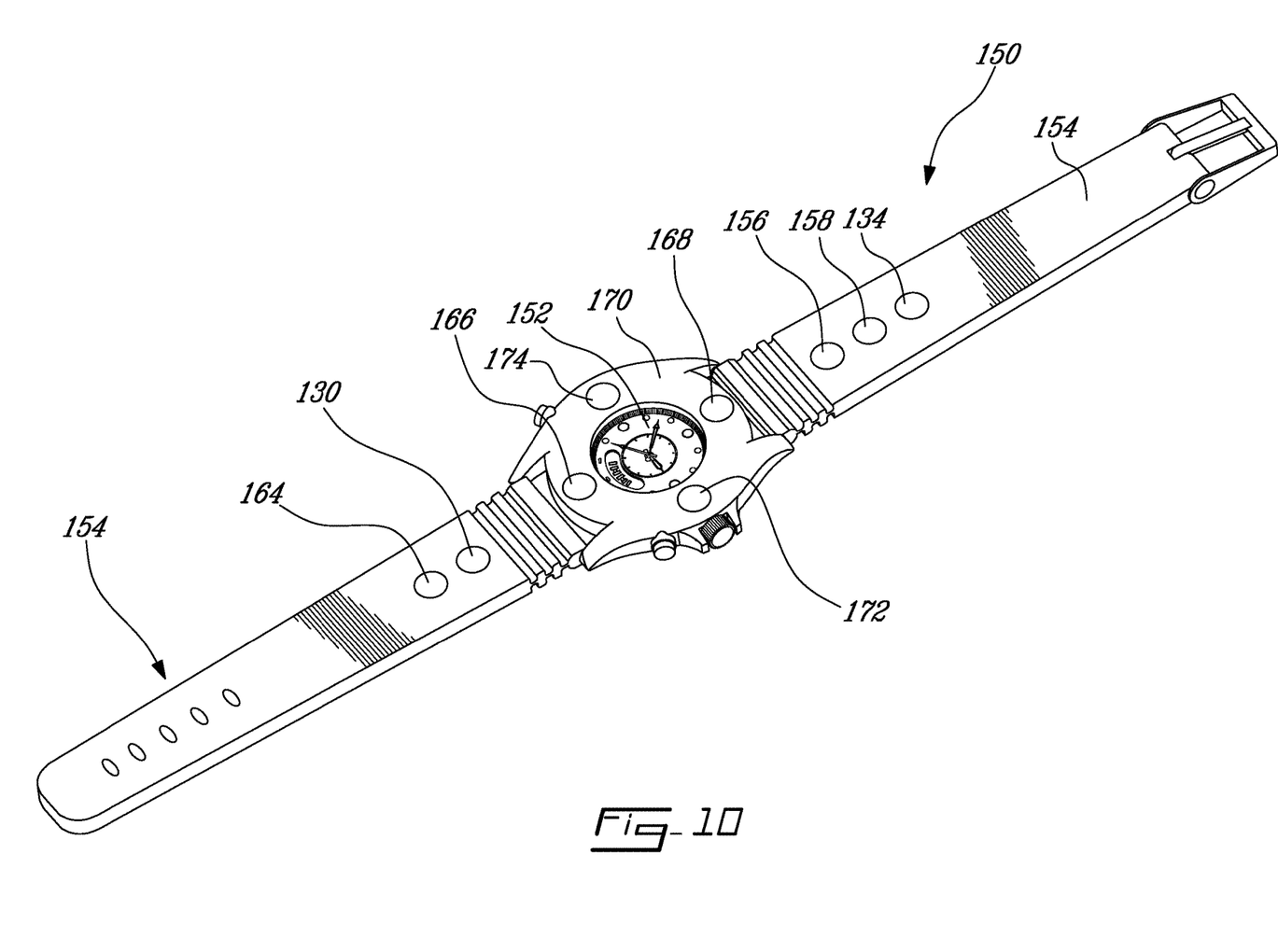
FIG. 10 illustrates an embodiment of a wrist assembly according to the present invention.

FIG. 10 illustrates an embodiment of a wrist assembly 150 of a wristwatch band type for locating a sensor unit. The bracelet part 154 integrates the sensors, including a 2-5 G accelerometer 156, a 50 G accelerometer 158, a gyroscope 134, a thermistor 130 and an impedance detector 164 for monitoring wearing of the assembly. The module 152 comprises a microphone 166, a 3D positioning unit 168, a help summon button 170, a battery 172 and a clock 174.

Data from a detector for monitoring wearing of the assembly (132, 164 in FIGS. 9 and 10 for example) may be integrated with data from the accelerometers and other sensors so as to further discriminate between events, between a fall of the monitored person and the monitored person merely dropping the neck assembly 120 or of the wrist assembly 150 on the floor for example.

Such system and method allows identification of critical activity levels, such as coma states, immobility over a period of time, breathing movements interruption, thereby allowing establishing a profile of daily nycthemeral activities of the monitored subject for example. Such profile may be used for detecting sudden variations, which may be significant of a decline in the monitored subject's well being, and provide information concerning the evolution of parameters of the profile of daily nycthemeral activities of the monitored subject, weighted according to the initial functional independence level of the monitored subject to permit assessment of functional independence variations.

Figure 12:
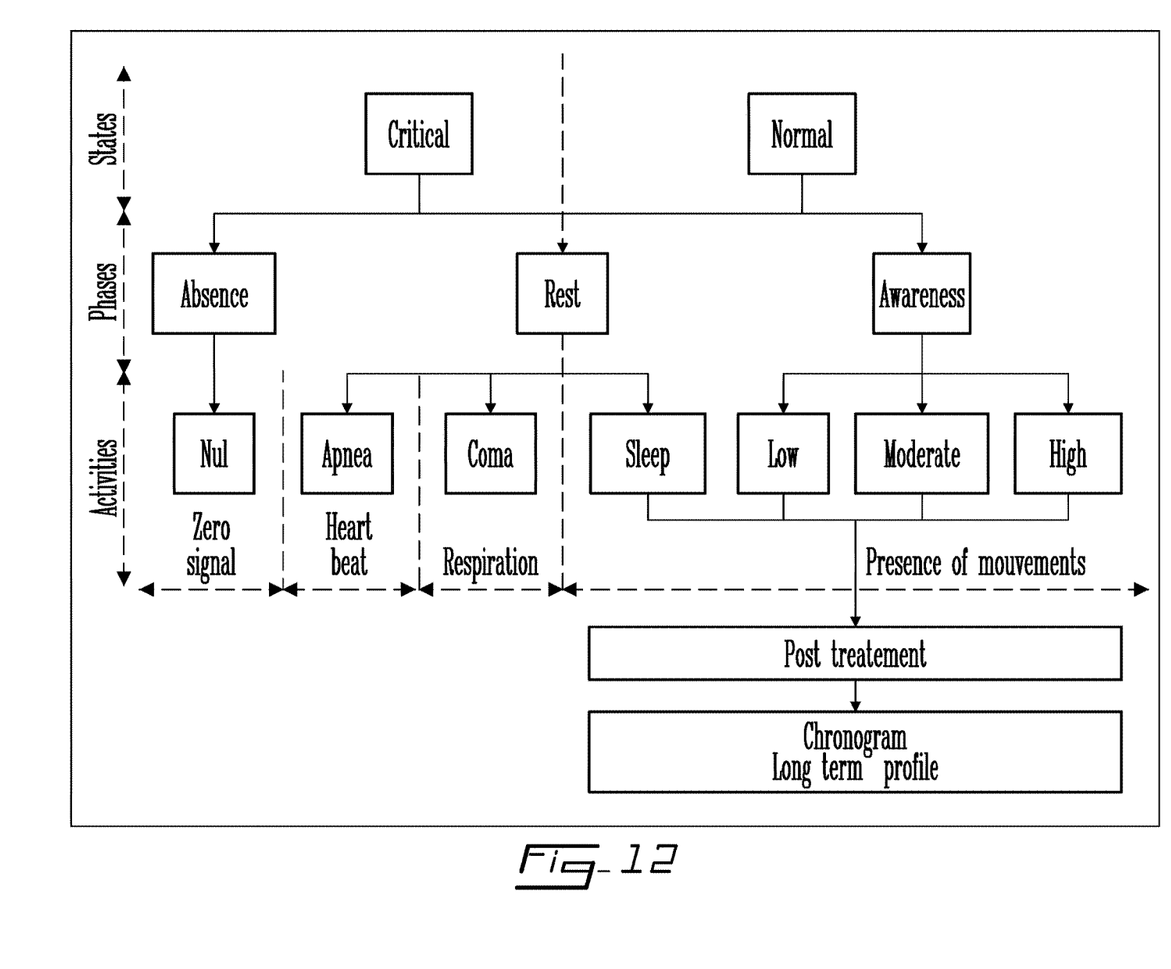
FIG. 12 is a diagram showing the results obtained by a method according to the present invention.

Acceleration, velocity and/or position signals sampled on at least one sensing assembly comprising a sensor unit located on the trunk, and, optionally, a sensor unit located on the wrist of the monitored subject, each sensing assembly comprising an accelerometer and optionally a gyroscope and/or a piezo-film, may be used to provide a representation for the behavior of the monitored subject through activity levels (see FIG. 12).

Figure 11:
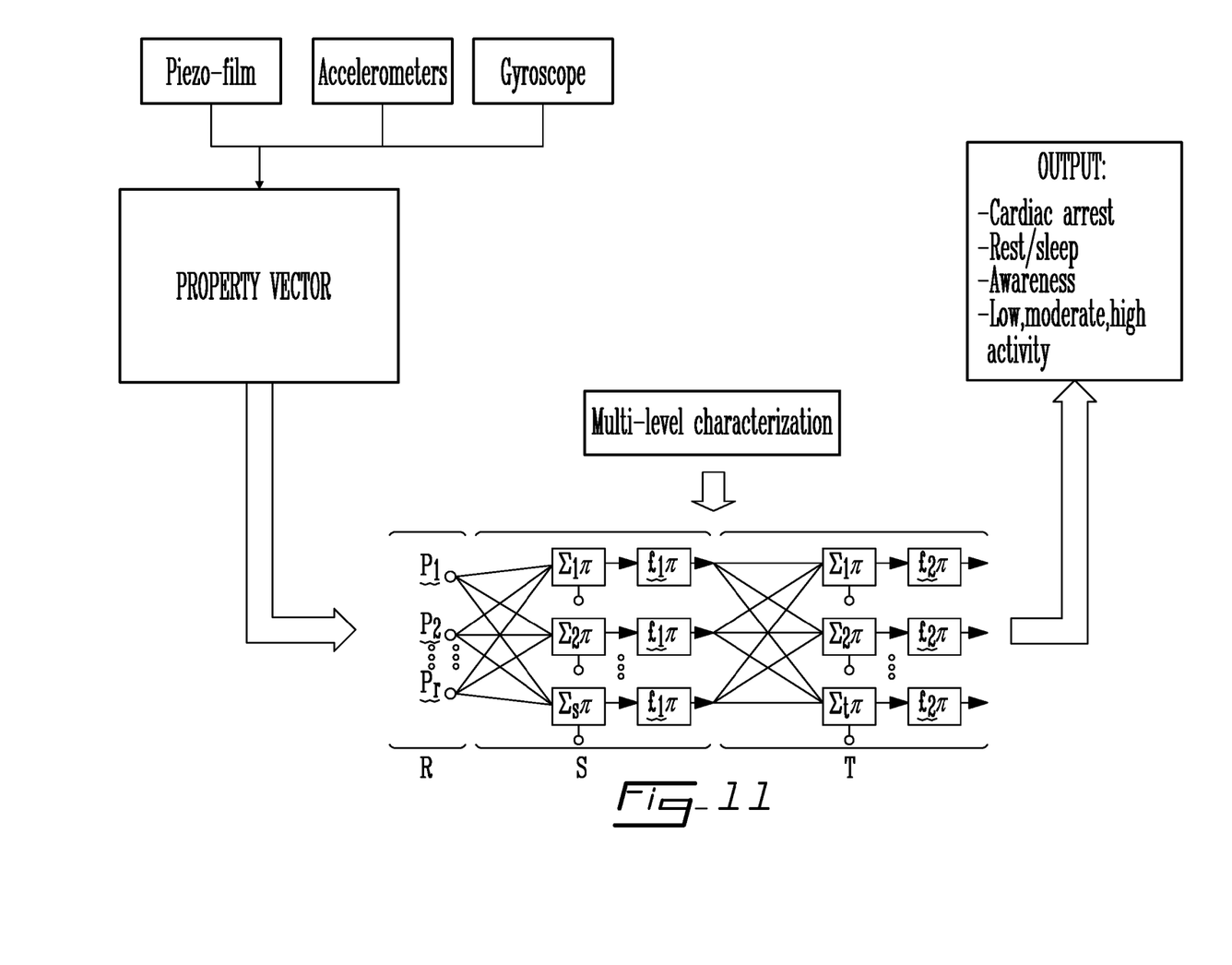
FIG. 11 is a flowchart of a further embodiment of a method according to the present invention.

The activity levels are characterized using indicators (such as NE, NM, INC discussed hereinabove for example) on the body posture of the monitored subject and of any change in her-his position in her-his environment, of the velocity and quantity of movements of each part of her-his body wearing a sensor unit, obtained from processing the acceleration, velocity and/or positional signals collected by the sensing assembly. As described hereinabove, these indicators or property vectors are analyzed to yield the state, phase of state and activities of the monitored subject, and the evolution thereof during a predetermined period of time (see FIG. 11).

As illustrated in FIG. 12, the state of the monitored subject may be assessed between a critical state corresponding to a problem or an activity level indicating a potentially deficient well being, and a normal state. In each case, an absence of movement as indicated by the absence of movement detection, may be interpreted as a defective system or as the death of the monitored subject, while slow heart beat, breathing movements and minimal body movements may be interpreted as representative of a rest phase of the monitored subject, and body or member movements, as characterized by their frequency, velocity and orientation, may be evidence of an awareness phase of the monitored subject. In each of these phases, different activity levels may then be assessed, from null in the phase of absence of detection), to apnea (heart beats are detected), coma (breathing is detected), and sleep (movements are detected) in the rest phase, and to low, moderate and high activity levels (movements are detected) in the awareness state.

The frequency analysis of signals collected at the base of the neck of the monitored subject yields a quantitative assessment of the movement of the monitored subject, including the variations of this quantity of movements during short periods of time.

The analysis of signals collected at the wrist of the monitored subject may be combined to yield a qualitative assessment of this movement by incorporating angular velocity measurements and positional measurement in space (x, y, z). The combined analysis of signals emitted in the region of the base of the neck and of signals emitted in the region of the wrist yield an accurate activity profile and efficient positioning along the vertical axis (z). This in turn results in a possible identification of the very room in which an event occurs (bathroom, kitchen, bedroom etc. . . . ) by cross-correlation, and therefore to an increasingly efficient monitoring system, since allowance levels may be predetermined individually for each room of the subject's habitat, considering for example that the subject detected lying on her-his bed in her-his-bedroom and sleeping is reasonably a normal event.

Therefore the present system and method allow monitoring a subject very precisely in relation to her-his individual functional independence level as well as his-her environment.

Although embodiments were illustrated given hereinabove in relation to a human, the present system and method may efficiently be applied for monitoring a range of subjects, including for example farm animals, domestic pets etc. . . .

Although the present invention has been described hereinabove by way of embodiments thereof, it may be modified, without departing from the nature and teachings of the subject invention as defined in the appended claims.

What is claimed is:

1. A method for monitoring activity and fall of a subject, comprising:
   measuring acceleration data using a human kinetic sensor (HKS) assembly placed at an upper trunk of the subject
      said HKS assembly comprising a sensing unit configured for sensing a low G acceleration at a low frequency sampling range and a high G acceleration at a high frequency sampling range,
      said acceleration data being correlated to the spine of the subject due to a placement of the sensing unit at the upper trunk of the subject to yield behaviour indicators and threshold levels associated with characteristics the subject and an activity nature, state and level for a given environment and time;
   processing the acceleration data in the low G acceleration into data reflecting a three-dimensional vectorial position of the upper body of the subject as being directly correlated with an orientation of the entire spine and body of the subject due to said placement of the HKS assembly at the upper trunk of the subject to yield a posture for a range of human activities in the given environment and time;
   processing the acceleration data in the low G acceleration to:
      recognize an activity of the subject,
      determine a phase, a state of the phase, levels of file activity over time, thresholds and controlled parameters range for the subject and the given environment and time,
      yield movement level, energy level and critical level threshold, and
      control parameters range for the subject and the given environment and time: and
   processing the acceleration data in the high G acceleration and low G acceleration into data identifying a fall event and determining the severity of the fall event based on at least one of said thresholds or said controlled parameters.

2. The method of claim 1, further comprising remotely monitoring the HKS assembly worn by the subject under a wireless sensor area network (WISAN) to detect emergency situations that require support for the subject.

3. The method of claim 1, further comprising at least one sensing assembly in the environment of the subject for sensing at least one parameter of the environment, said parameter comprising, presence of the subject in a zone covered by a wireless sensor network area (WISAN), said at least one sensing assembly being integrated in a communication base that manages the WISAN and links to an external network and a server.

4. The method of claim 1, wherein the HKS assembly is placed at the base of the back of the neck of the subject.

5. The method of claim 1, littler comprising combining measurements and analysis of other sensors worn by the subject to the measured acceleration data to perform activity profiling, efficient positioning and allowance level for individual characteristics and locations.

6. The method of claim 1, further comprising determining spatial displacements and variations of position of the upper trunk of the subject based on the processed acceleration data measured by said sensing unit in the low G acceleration to yield orientation of the upper body of the subject in space.

7. The method of claim 1, wherein the HKS assembly further includes a wearing sensor for confirming the subject is wearing the HKS assembly.

8. The method of claim 1, further comprising monitoring a usage of the HKS assembly over time or reminding the subject to wear the HKS assembly.

9. The method of claim 1, farther comprising
   positioning a wrist sensor at an arm of the subject, said wrist sensor being configured for sensing the low G acceleration at the low frequency sampling range and a high G acceleration at the high frequency sampling range of the arm of the subject to assess an activity level of the subject, said arm being preferentially the writing arm or the subject.

10. The method of claim 9, further comprising measuring and processing the low G acceleration and the high G acceleration to determine a velocity, movement and position in space of the arm.

11. The method of claim 10, further comprising using the wrist sensor in combination with the HKS assembly for activity assessment and recognition and to yield the phase, the state of the phase and the levels of activity over time of the subject for the given environment and time.

12. The method of claim 1, further comprising defining and characterizing activity levels using the processed acceleration data and indicators (NE, NM, INC) from of each part of the body of the subject wearing a sensor unit body posture, and a change in a position of the subject in the environment over time.

13. The method of claim 1, further comprising determining a natural posture of the subject by correcting the processed acceleration data for the subject at rest with an offset correcting internal errors of the sensing unit and a positioning of the sensing unit on the body of the subject.

14. The method of claim 1, further comprising determining whether the subject is lying on the floor, lying on a bed, seated, kneeling down, or standing up to assess the levels of activity of the subject or identify and yield a severity indicator for the subject.

15. The method of claim 1, further comprising using an on-bed presence detector to manage allowance and threshold of critical level for lying posture of the subject in the given environment and time.

16. The method of claim 12, further comprising:
    determining spatial displacement and variations of a position of the upper trunk of the subject based on the processed acceleration data measured by said sensing unit in the low G acceleration to yield a movement level indicator (NM) of the subject; and
    determining movement intensity of the subject over a period time based on the processed acceleration data measured by said sensing unit in the low G acceleration and the high G acceleration to yield an energy level indicator (NE) of the subject.

17. The method of claim 1, further comprising, defining a gain (KM) for a movement level and a gain (KE) for the energy level of the subject, said KM and KE being used as weighting factors to adjust indicator values to critical levels for characteristics of the subject and the given environment and time.

18. The method of claim 1, further comprising identifying the fall event of the subject by measuring a gradient and amplitude of shock waves based on the processed acceleration data measured by said sensing unit in comparison to an adjustable threshold.

19. The method of claim 1, further comprising determining the severity of the fall event as a fall indicator, said fall indicator using the sum of values of amplitudes measured during the fall event assessing impacts and indicating a severity value that assesses the fall event.

20. The method of claim 1, further correlating a heartbeat, a respiration rate and an upper body movement of the subject to the processed acceleration data to assess activity levels and critical states corresponding to a problem or activity levels indicating a potentially deficient well-being or normal sate of the subject.

21. The method of claim 1, further comprising determining a critical level for an awareness phase of the subject in cross correlation with heartbeats and a respiration rate of the subject to differentiate a normal state of the subject from a critical state, the awareness phase comprising:
    a null phase indicating no heartbeat and no respiration;
    an apnea phase indicating heartbeats and no respiration;
    a coma phase indicating hearthbeats and respirations but posture and movement levels incoherent for the given environment and time;
    rest phase;
    faintness phase;
    low to high level of activity; and
    hyperactivity.

22. A method for monitoring sleep activity of a subject, comprising
    measuring acceleration data from at least one kinetic sensor being worn by the subject and a sleep sensor located where the subject is sleeping to yield movement levels of the subject, said kinetic sensor comprising at least one of:
        a sensing unit configured for sensing acceleration data comprising a low G acceleration at a low frequency sampling range and a high G acceleration at a high frequency sampling range, said acceleration data being correlated to the spine of the subject due to a placement of the sensing unit at the upper trunk of the subject to yield behaviour indicators and threshold levels associated with characteristics the subject and an activity nature, state and level for a given environment and time, and
        a wrist sensor located at an arm of the subject, said wrist sensor being configured for sensing acceleration data comprising the low G acceleration at the low frequency sampling range and the high G acceleration at the high frequency sampling range of the arm of the subject to assess an activity level of the subject.

* * * * *

UNITED STATES PATENT AND TRADEMARK OFFICE
CERTIFICATE OF CORRECTION

PATENT NO.        : 10,299,704 B2
APPLICATION NO.   : 15/446503
DATED             : May 28, 2019
INVENTOR(S)       : Cloutier et al.

Page 1 of 1

It is certified that error appears in the above-identified patent and that said Letters Patent is hereby corrected as shown below:

In the Claims

Claim 5, Column 8, Line 37, "littler comprising" should read -- further comprising --

Signed and Sealed this
Twenty-third Day of July, 2019

Andrei Iancu
*Director of the United States Patent and Trademark Office*